United States Patent [19]

Buechler et al.

[11] 4,178,640

[45] Dec. 18, 1979

[54] WRIST PROSTHESIS

[76] Inventors: Ulrich H. Buechler, 3037 Stuckishaus, Halen 50, Switzerland; Dennis B. Phelps, 4517 Vieja Dr., Santa Barbara, Calif. 93110; John A. Boswick, Jr., 4502 S. Vine Way, Englewood, Colo. 80110

[21] Appl. No.: 880,397

[22] Filed: Feb. 23, 1978

[51] Int. Cl.$^2$ ............................................. A61F 1/24
[52] U.S. Cl. ................................. 3/1.91; 128/92 C
[58] Field of Search ............................ 3/1.9–1.913; 128/92 C, 92 A

[56] References Cited

U.S. PATENT DOCUMENTS

| | | | |
|---|---|---|---|
| 3,852,831 | 12/1974 | Dee | 3/1.91 |
| 3,869,729 | 3/1975 | Attenborough | 3/1.91 |
| 3,909,853 | 10/1975 | Lennox | 3/1.91 |
| 4,038,704 | 8/1977 | Ring | 3/1.91 |
| 4,040,130 | 8/1977 | Laure | 3/1.91 |
| 4,059,854 | 11/1977 | Laure | 3/1.91 |
| 4,063,314 | 12/1977 | Loda | 3/1.91 |

FOREIGN PATENT DOCUMENTS

| | | | |
|---|---|---|---|
| 2501128 | 7/1976 | Fed. Rep. of Germany | 3/1.911 |
| 2288509 | 5/1976 | France | 3/1.911 |

OTHER PUBLICATIONS

"Total Arthroplasty of the Wrist to Relieve Pain and Increase Motion" by R. L. Linscheid et al., *Geriatrics*, Apr. 1976, pp. 48–52.

"The Development of a Total Wrist Arthroplasty" by Robert G. Volz, Clinical Orthopaedics & Related Research, No. 116, May 1976, pp. 209–214.

"Total Wrist Arthroplasty: A Preliminary Report" by R. D. Beckenbaugh et al., The Journal of Hand Surgery, vol. 2, No. 5, pp. 337–344, Sep. 1977.

*Primary Examiner*—Ronald L. Frinks
*Attorney, Agent, or Firm*—Sherman and Shalloway

[57] ABSTRACT

A prosthesis for the wrist joint and other joints which includes a carpal component having a base for cooperation with a radial component. The base is formed in the shape of a half-toroid, each end of the toroid integrally forming an intra-medullary pin for insertion into the medullary canal of the metacarpals with acrylic cement or equivalent gap-filling medium. The radial component of the prosthesis has a seat which is generally concave for receiving a side of the base of the carpal component. The seat includes a pair of adjacent concave surfaces tapering into cylindrical shafts, the toroidal base located between the shafts. A ridge is formed between the concave surfaces allowing the toroidal base to ride upon the ridge and rotate front to back and/or slide side to side. A tapered, notched stem extends from the seat for insertion into the medullary canal of the radius.

7 Claims, 12 Drawing Figures

WRIST PROSTHESIS

BACKGROUND OF THE INVENTION

1. Field of the Invention

The invention generally relates to joint prosthesis devices and, more specifically, involves a wrist joint prosthesis for human implantation and use.

2. Description of the Prior Art

Although wrist joint prosthetic devices have been proposed in the prior art, they have not always been entirely successful. This is due to the fact that the wrist joint is relatively more complex than most joints in that it comprises a greater number of bones which cooperate to provide a plurality of distributed articular capabilities.

Insofar as the wrist joint is regarded as being one of the more likely joints to be affected by arthritic conditions which reduce articular function, the need for effective wrist joint prosthesis is great. Further, a wrist joint prosthesis can be used to replace a wrist joint which does not provide complete function or otherwise adversely affects the entire wrist and utility of the relevant hand.

The Meuli design for a wrist joint prosthesis is a ball-and-socket joint. The distal component of the Meuli prosthesis consists of a hemispherical cup with two attached stems that fit through the remnant of the carpal row into the second and third metacarpals. The proximal component consists of a single peg at the wrist level with two stems that insert into the radial intermedullary cavity. A polyethylene ball is placed on the peg and is reduced into the distal hemispherical cup, providing a range of motion in flexion, extensions, abduction, adduction, and rotation. The rotation is not entirely desirable. The stems of the proximal and distal components are malleable so that they may be adjusted.

Another prosthesis, by Voltz, has only two degrees of freedom and thus behaves as a universal joint. Flexion and extension occur in one plane, and radial abduction and ulnar abduction occur in the second plane. This is somewhat more physiologic but causes additional difficulties in design.

SUMMARY OF THE INVENTION

The wrist prosthesis of this invention is comprised of a first or carpal component and a second or radial component. The carpal component has a curved tubular base which approximates the shape of a half toroid. Each end of the half toroid integrally is shaped into an intramedullary pin for insertion into the medullary canal of the metacarpals. The radial component has a generally concave seat which accepts the base of the carpal component. The radial component has a tapered stem with notches therein. The stem is offset on the radius side, i.e. toward the radius and superior to the center line of the base. The seat has first and second adjacent concave surfaces tapering into cylindrical shafts. A ridge is formed between the concave surfaces on which the toroidal base rides allowing front to back rotational movement and/or side to side sliding movement of the carpal component with respect to the radial component.

It is an object of this invention to provide a wrist prosthesis having a radius articulating surface offset on the outer side and inferior to the center line of the stem which fits into the medullary canal of the radius, thereby providing correct anatomical positioning.

It is another object of this invention to provide a wrist prosthesis which allows circumduction motion of the wrist for fine translations in wrist positioning in three planar motions: flexion-extension, radioulnar abduction at the radiocarpal and intercarpal joints, with pronation and supination occurring longitudinally within the forearm and transmitter through the proximal and distal radioulnar joints.

It is a further object of this invention to provide a wrist prosthesis which provides adequate range of motion and radial or ulnar deviation as well as extension or flexion, but does not allow for unlimited range of movement.

It is a further object of this invention to provide a wrist prosthesis which has a radial component having one stem which properly locates the prosthesis in the medullary canal.

It is yet another object of this invention to provide a wrist prosthesis which has a carpal component including intramedullary pins which diverge for insertion into the medullary canal of the metacarpals.

Yet another object of this invention is to provide a total wrist prosthesis which has components allowing for distraction rather than transmission of tensile forces across the prosthesis.

Another object of this invention is to provide a wrist prosthesis which has left and right components which are required to obtain the proper anatomical positioning.

It is an object of this invention to provide a total wrist prosthesis which can be used to replace the human wrist joint with minimal bone resection and provide a system which is equivalently effective to the human wrist joint.

It is an object of this invention to provide a total wrist prosthesis which allows stability of the hand on the radius and preserves the rigidity of the second and third metacarpals.

It is also an object of this invention to preserve the mobility of the basilar joints of the thumb and the fourth and fifth metacarpals without sacrificing their mobility.

It is a final object of this invention to provide a total wrist prosthesis which allows an adequate range of motion and can transmit a strong rotary force or torque to the hand.

BRIEF DESCRIPTION OF THE DRAWING

These features and objects of the invention, as well as others will become apparent to those skilled in the art by referring to the drawing in which.

DETAILED DESCRIPTION OF THE INVENTION

Figure 7:
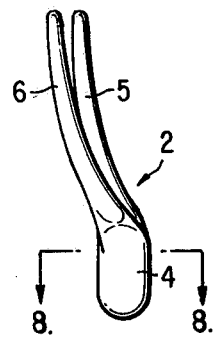
FIG. 7 is a right side view of the carpal component.
Figure 9:
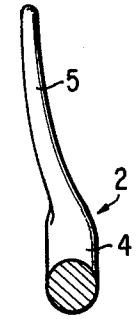
FIg. 9 is a sectional view of the carpal component taken along lines 9—9 of FIG. 6.
Figure 8:
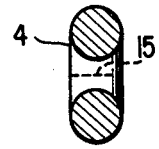
FIG. 8 is a sectional view of the carpal component taken along lines 8—8 of FIG. 7.

The total wrist joint prosthesis generally referred to by reference character 1 is comprised of a first component which is the carpal component 2 and a second component which is the radial component 3. The purpose of the prosthesis is to replace a joint between a first bone structure having first medullary canals and a second bone structure having a second medullary canal. The carpal component 2 is structured from a base portion 4 which has a tubular shape with a curved longitudinal axis 4a. In the preferred embodiment, the tubular shape is a half-toroid having a notch 4b which aids in the seating of the carpal component 2. Each end of the tubular base 4 integrally terminates in intramedullary pins 5 and 6. These anatomical diverging pins are adapted for insertion into the medullary canals of the metacarpals with acrylic cement or equivalent gap-filling medium. By referring to the right side view illustrated in FIG. 7, it can be noted that the diverging pins 5 and 6 are curved toward the front and slightly offset from each other to allow proper anatomical positioning.

The carpal component with its intramedullary pins 5 and 6 provides a system in which the hand is able to provide the normal grasping motion because the second and third metacarpals are held rigidly in line with the distal carpal row while the ulnar two digits and the thumb have a conical mobility about the fixed second and third metacarpal axes. This allows the palm and fingers to adapt spacially to the varying contours of objects to be grasped. For successful hand function, it is necessary to retain the stability of the two central metacarpals by use of the intramedullary pins 5 and 6.

Figure 1:
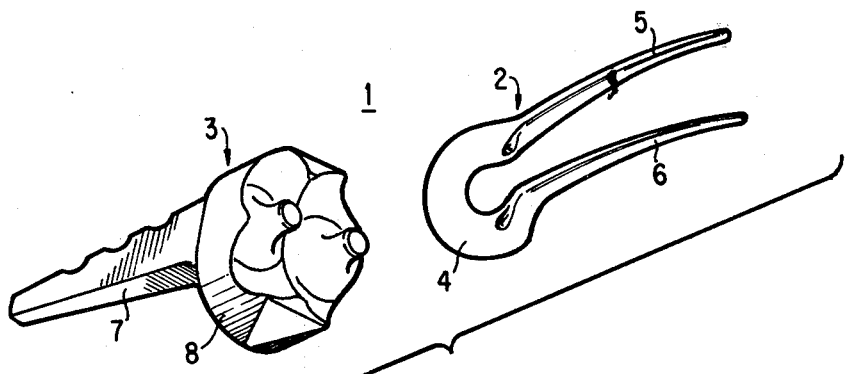
FIG. 1 is an oblique top view of the carpal component located over the radial component of a wrist prosthesis for the right wrist.
Figure 3:
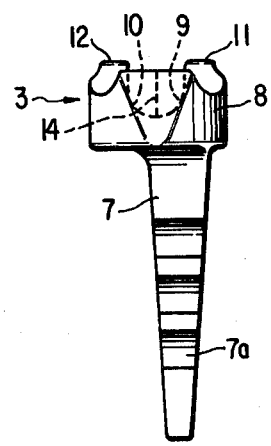
FIG. 3 is a left side view of the radial component.
Figure 2:
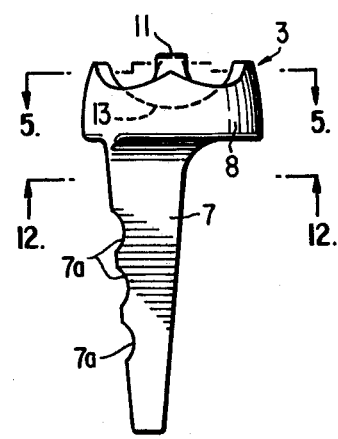
FIG. 2 is a top view of the radial component.
Figure 4:
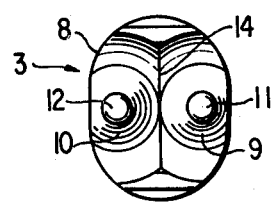
FIG. 4 is a front view oriented 90° from the horizontal axis of the radial component.
Figure 5:
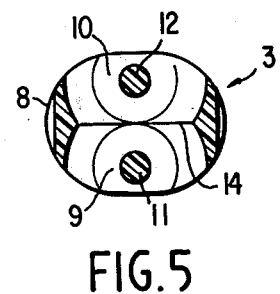
FIG. 5 is a sectional view of the front portion of the radial component taken along 5—5 of FIG. 2.
Figure 6:
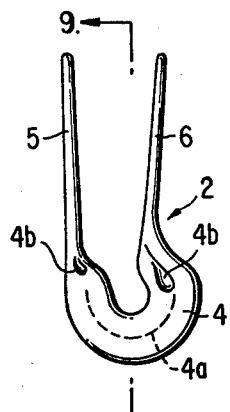
FIG. 6 is a top view of the carpal component.
Figure 12:
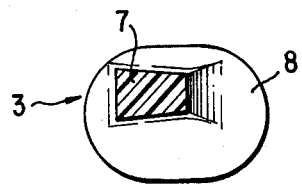
FIG. 12 is a sectional view of the stem of the radial component taken along lines 12—12 of FIG. 2.

The radial component 3 has a stem 7 which is offset on the radius side, i.e. toward the radius, as can be seen by referring to FIG. 2, and is superior to the center line of the seat 8, as can be seen by referring to FIG. 3. This offset feature is also illustrated in FIG. 12, wherein it is shown that the cross-section of the stem is generally trapezoidal. The stem 7 is tapered away from a base 8 and includes notches 7a therein. The stem 7 is inserted into the medullary canal of the radius with acrylic cement such as methylmethacrylate or equivalent gap-filling medium and the notches 7a aid in the fixation of the radial component 3 to the radius.

The seat 8 of the radial component 3, in the preferred embodiment, includes 2 adjacent concave surfaces 9 and 10 which taper into cylindrical shafts 11 and 12. The generally concave surface of the seat 8 can be best appreciated by referring to the dotted line indicated by reference character 13 in FIG. 2. The purpose of the two cylindrical shafts 11 and 12 is to prevent rotation within the wrist joint itself. Such wrist joint rotation is neither necessary nor desirable as long as the rotary capabilities of the forearm are intact. If such rotation is possible and there is no mechanism, such as the shafts 11 and 12, for blocking rotation, the application of twisting or turning forces through the wrist to the hand becomes difficult.

Figure 10:
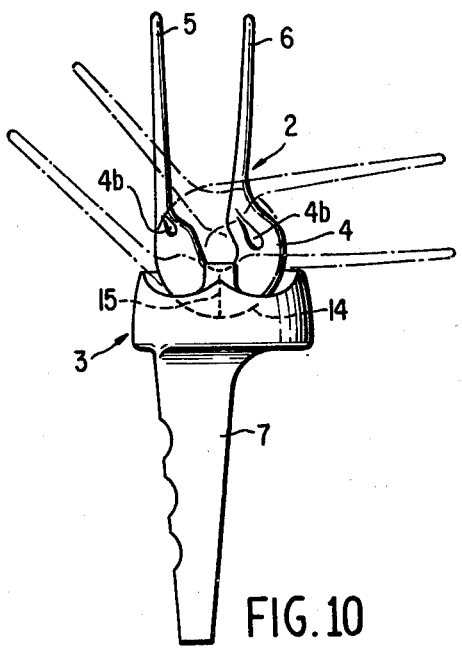
FIG. 10 is a top view of the radial component with the carpal component seated in the upright position and shown in phantom in the right-most and left-most position.
Figure 11:
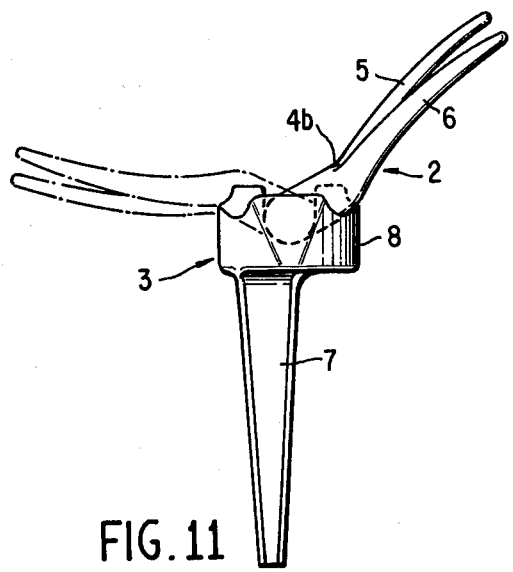
FIG. 11 is a right side view of the radial component with the carpal component seated in the front-most position and shown in phantom in the rear-most position.

Actually, the two concave surfaces 9 and 10 form a ridge 14 therebetween. In the preferred embodiment, the ridge 14 has a semicircular shape approximating the shape and longitudinal axis of the side of the tubular base 4. By referring to FIG. 10, it is apparent that the tubular base 4 of the carpal component when inserted into the seat 8 of the radial component rides along the ridge 14. This allows rotation of the carpal component 2 about a central transverse cross-section 15 of the base 4 from the front to the rear and vice versa, as indicated by FIG. 11 wherein the carpal component 2 is illustrated in the front-most position and in phantom in the rear-most position. The ridge feature also limits articulating motion along the longitudinal axis of the carpal component 2 from side to side, as can be noted by referring to FIG. 10 wherein the carpal component 2 is shown in phantom in the right-most and left-most positions.

Holes are rasped or broached through the retaining distal portion of the trapezoid and capitate and into the intramedullary cavities of the second and third metacarpals. Rasped or broached holes are also made in the distal radius, and after some enlargement, the components are then fitted into place, being adjusted as necessary. The components are cemented into place after they have been fitted satisfactorily. Considerable care must be exercised to be certain that they are adequately seated and are displaced toward the palm far enough so that there is a satisfactory moment arm for the radial wrist extensors.

The presently preferred choice of materials for construction of the wrist prosthesis is a metal such as an appropriate cobalt-chromium-molybdenum or stainless steel alloy for the carpal component, and a plastic material such as high density polyethylene for the radial component.

The wrist prosthesis illustrated is for the right wrist. The left wrist prosthesis is of the same configuration with reversed symmetry, i.e. a mirror image of the carpal component 2 and the radial component 3.

Various changes may be made in the details of the invention, as disclosed, without sacrificing the advantages thereof or departing from the scope of the appended claims. Furthermore, although the present invention has been disclosed and discussed with particular regard to its exceptional advantages in terms of a total wrist prosthesis, it may be understood that the invention may be employed in several applications as a joint prosthesis.

For example, it is contemplated that the carpal component may be structured with a symmetrical tubular base and the ends of the base integrally form a single pin. Alternatively, the seat of the radial component may be a concave surface corresponding to the shape of the side of the tubular base. The seat can include stops similar to the cylindrical shafts to prevent axial rotation but such limited action may not be necessary for certain joint applications.

What is claimed is:

1. A prosthesis for replacing a joint between a first bone structure having first medullary canals and a second bone structure having a second medullary canal, said prosthesis comprising:
(A) a first component having a tubular base with a curved longitudial axis, said base having ends terminating into intermedullary pins for insertion into the first medullary canals; and (B) a second component having a generally concave seat for receiving a side of said tubular base and an intramedullary stem extending from said seat for insertion into the second medullary canal.

2. The prosthesis of claim 1 wherein said seat of the said second component further comprises first and second adjacent concave surfaces tapering into cylindrical shafts for preventing axial rotation of said first component with respect to said second component, said tubular base located between said shafts.

3. The prosthesis of claim 2 wherein said first and second adjacent concave surfaces form a ridge having a semi-circular shape approximating the shape of said tubular base, said tubular base located on said ridge thereby allowing rotational movement of said first component about a central transverse cross-section of said base and sliding movement along the longitudinal axis.

4. The prosthesis of claim 1 wherein said base is a half-toroid.

5. The prosthesis of claim 1 wherein said stem is offset from a central point of said seat, said stem being tapered.

6. The prosthesis of claim 1 wherein said pins are integrally connected to said ends of said tubular base, said pins having a curvature corresponding to the curvature of the medullary canals of the metacarpals.

7. The prosthesis of claim 1 wherein said pins diverge.

* * * * *